United States Patent [19]
Lee et al.

[11] Patent Number: 5,621,188
[45] Date of Patent: Apr. 15, 1997

[54] AIR PERMEABLE ELECTROMAGNETIC SHIELDING MEDIUM

[76] Inventors: Sang C. Lee; Bak H. Lee, both of 352 Stanwich Rd., Greenwich, Conn. 06830

[21] Appl. No.: 239,331

[22] Filed: May 6, 1994

[51] Int. Cl.⁶ .................................................. H05K 9/00
[52] U.S. Cl. .............................. 174/35 MS; 250/516.1; 250/519.1
[58] Field of Search ................ 174/35 R, 35 GC, 174/35 MS; 428/209, 910; 128/201.15; 2/2, 6.4, 6.7; 250/505.1, 515.1, 516.1, 519.1; 450/153; 138/127; 361/816, 818

[56] References Cited

U.S. PATENT DOCUMENTS

| | | | |
|---|---|---|---|
| 1,191,274 | 7/1916 | Brayton | 128/201.15 |
| 2,855,603 | 10/1958 | Zito | 2/2 |
| 2,857,525 | 10/1958 | Ferdon | 250/519.1 |
| 3,030,628 | 4/1962 | Crosson | 2/433 |
| 3,164,840 | 1/1965 | Reynolds | 2/2 |
| 3,256,442 | 6/1966 | Sedlak | 250/519.1 |
| 3,265,898 | 8/1966 | Lehmer | 250/437 |
| 3,310,053 | 3/1967 | Greenwood | 450/153 |
| 3,394,260 | 7/1968 | Phipps | 250/516.1 |
| 3,465,153 | 9/1969 | Libby | 250/395 |
| 3,967,129 | 6/1976 | Winkler | 250/517.1 |
| 3,984,696 | 10/1976 | Collica et al. | 250/519.1 |
| 3,996,620 | 12/1976 | Maine | 2/2 |
| 4,021,862 | 5/1977 | Glasser et al. | 2/431 |
| 4,024,405 | 5/1977 | Szot | 250/516.1 |
| 4,029,969 | 6/1977 | Kondo et al. | 307/10.1 |
| 4,378,009 | 3/1983 | Fearnside et al. | 138/127 X |
| 4,451,739 | 5/1984 | Christ et al. | 250/506.1 |
| 4,471,015 | 9/1984 | Ebneth et al. | 428/195 |
| 4,542,076 | 9/1985 | Bednarz et al. | 428/624 |
| 4,613,820 | 9/1986 | Edelstein et al. | 324/318 |
| 4,662,967 | 5/1987 | Bogan et al. | 174/35 MS X |
| 4,684,762 | 8/1987 | Gladfelter | 174/36 |
| 4,703,133 | 10/1987 | Miller | 174/35 GC |
| 4,853,790 | 8/1989 | Dickie | 348/819 |
| 4,857,668 | 8/1989 | Buonanno | 174/35 GC |
| 4,938,233 | 7/1990 | Orrison, Jr. | 128/849 |
| 5,014,160 | 5/1991 | McCoy, Jr. | 361/818 |
| 5,022,099 | 6/1991 | Walton | 2/410 |
| 5,023,394 | 6/1991 | Watanabe et al. | 174/35 R |
| 5,038,047 | 8/1991 | Still | 250/516.1 |
| 5,073,984 | 12/1991 | Tone et al. | 2/2 |
| 5,115,140 | 5/1992 | Rodriguez | 250/516.1 |
| 5,118,925 | 6/1992 | Mims et al. | 250/214 VT |
| 5,122,619 | 6/1992 | Dlubak | 174/35 R |
| 5,134,245 | 7/1992 | Katz | 174/35 R |
| 5,140,710 | 8/1992 | Rademacher | 2/432 |
| 5,153,378 | 10/1992 | Garvy, Jr. | 5/512 X |
| 5,155,316 | 10/1992 | Chiu | 219/634 |
| 5,180,513 | 1/1993 | Durand | 252/62.55 |
| 5,235,492 | 8/1993 | Humbert et al. | 361/818 |
| 5,244,708 | 9/1993 | Tsuchida et al. | 428/77 |
| 5,250,342 | 10/1993 | Lang et al. | 428/138 |
| 5,262,737 | 11/1993 | Siverling | 333/12 |
| 5,278,351 | 1/1994 | Herrick | 174/35 R |
| 5,285,007 | 2/1994 | Delucca et al. | 174/35 R |

FOREIGN PATENT DOCUMENTS

WO87/00342  1/1987  WIPO .

OTHER PUBLICATIONS

"Catching the Light," Arthur Zajonc, Feb. 1993, pp. 144–151.
"Electromagnetic Compatbility by Design," Oren Hartal, 1991, pp. 161, 215.

*Primary Examiner*—Bot L. Ledynh
*Attorney, Agent, or Firm*—Eric Oliver

[57] ABSTRACT

A shielding medium using a multi-layered construction for protection of an object such as the human body, with each layer containing a plurality of geometrically shaped objects, that appears to the EMFs as a continuous, solid plane, but retains open spaces around the objects for ambient air to circulate. As a result of this construction, the unique shielding medium affords excellent protection against both the electric and magnetic field components of EMFs without sacrificing the comfort of the user (or heat dissipation of the source).

5 Claims, 9 Drawing Sheets

AIR PERMEABLE ELECTROMAGNETIC SHIELDING MEDIUM

BACKGROUND OF THE INVENTION

The present invention is directed to the field of electromagnetic shielding. More specifically, the invention is directed to an electromagnetic shielding medium which provides high shielding effectiveness with adequate air permeability.

All electrically energized devices radiate electromagnetic fields (EMFs) consisting of electrical and magnetic components. In today's society, human beings are exposed to such fields in almost everything they do. The electric clock on the nightstand emits EMFs, as does the microwave oven in the kitchen, the electric shaver in the bathroom, the television set in the living room, the personal computer in the den or office, the portable wireless communications devices (e.g., cellular telephones) used in the car or on the street, as well as the high voltage powerlines running underground or overhead. (The number and variety of different sources of EMFs are too numerous to recite herein.)

One of the first studies, conducted in the Soviet Union 20 years ago, suggested a link between exposure to electric fields and certain chronic afflictions such as headaches, fatigue and nausea. In 1979, the results of a major epidemiological study of EMFs conducted in the United States were published. They seemed to show an association between exposure to EMFs from powerlines and increased incidence of childhood cancer, though serious questions have since arisen about the methodology used.

In 1988, the Kaiser-Permanente Medial Care Program, concluded a study that found that pregnant women who used video display terminals (VDTs) for more than 20 hours a week during the first trimester were almost twice as likely to have miscarriages as other working women. Other studies have established that exposure to certain levels of EMFs does produce measurable physiological effects in humans. These include changes in calcium flow from cell membranes, which can affect cell division and reproduction. Researchers also have noted effects on various endocrine tissues, as well as changes in DNA synthesis rates and RNA transmission patterns. These effects occur at certain combinations of electric and magnetic field strength.

Recently, Sweden completed a study that prompted its government National Board for Industrial and Technical Development to announce that it would henceforth act on the assumption that there is a connection between exposure to power-frequency magnetic fields and cancer in particular childhood cancer. Australia, the Commonwealth of Independent States, Japan, Poland, and the United Kingdom have also taken action to regulate exposure.

Eight States in the United States (i.e., California, Colorado, Florida, New Jersey, Maryland, Massachusetts, Texas and Wisconsin) have adopted policies or standards for EMF exposure. Many other states are holding hearings or are considering some form of regulation.

The United States Federal Government response, however, is mixed. In 1990, the Environmental Protection Agency (EPA) released a draft report which concluded that EMFs are probable or possible human carcinogens. A White House Report, on the other hand, issued in 1992 indicated that there was no convincing evidence in the published literature to support the possibility that exposure to EMFs is a demonstrable health hazard.

Despite the lack of a consensus regarding the ill effects on the human body of exposure to EMFs, there have been many previous attempts to shield the human body from exposure. For example, U.S. Pat. No. 3,164,840 to Reynolds introduced a protective garment used to shield the entire body from the effects of EMFs at very high frequencies. The protective garment was formed of a metal mesh layer of thin metallic wire sandwiched between two cloth layers. This garment, however, was unable to fully protect the human body because of the ability of the EMFs to penetrate the openings lea in the wire mesh.

U.S. Pat. No. 3,394,260 to Phipps employed an electrically conductive sheet made of aluminum connected to ground completely enclosing the body of the wearer. Although this garment did not have openings in the protective sheet for EMFs to penetrate, a special air blower was required to introduce a circulation of fresh air within the garment.

In addition to the deficiencies noted above, these prior art shields were too heavy and cumbersome (nor were they designed) to be used by people in their everyday lives.

Noticeable improvements, however, have recently been made in the prior art shields. Patent Cooperation Treaty (PCT) International Publication No. WO 87/00342 by Gordon discloses, for example, an improved radiation shield that utilizes a layer of light-weight material such as mylar with a thin layer of light metal such as aluminum. Similarly, U.S. Pat. No. 5,115,140 to Rodriguez discloses a protective shield in the form of a light-weight insert that could be placed inside a wearer's apparel. The insert is in the form of a thermoplastic sheet, such as vinyl, coated with a non-oxidizing conductive copper-based coating composition.

These recent improvements, unfortunately, do not provide the wearer with apparel that provides both adequate protection and maximum comfort. That is, these improvements, although seemingly protecting the wearer from the electrical field components of EMFs, fail to specifically address the problem of exposure to the low frequency magnetic field component of EMFs. Moreover, due to the uniform nature of the conductive coatings applied to the shields noted above, none of the shields provides a breathable or air permeable medium that would allow air to freely circulate through the apparel, thereby making the medium uncomfortable when worn for extended periods of time.

SUMMARY OF THE INVENTION

An object of the invention, therefore, is to provide an electromagnetic shielding medium that adequately protects an object such as the human body from electromagnetic fields while providing maximum comfort at the same time.

A further object of the invention is to provide a shielding medium that resists both the electrical and magnetic components of EMFs in the widest possible frequency ranges.

Yet another object of the invention is to provide a shielding medium that contains EMFs emanating from a source.

The foregoing and other objects, features, and advantages can be achieved in accordance with the invention by a shielding medium using a multi-layered construction, with each layer containing a plurality of geometrically shaped objects, that appears to the EMFs as a continuous, solid plane, but retains open spaces around the objects for ambient air to circulate. As a result of this construction, the unique shielding medium affords excellent protection against (or containment of) both the electric and magnetic field components of EMFs without sacrificing the comfort of the user (or heat dissipation of the source).

BRIEF DESCRIPTION OF THE DRAWINGS

The accompanying Drawings, which are incorporated in and constitute a part of this specification, illustrate preferred embodiments of the invention and, together with the description, serve to explain the principles of the invention, wherein.

DETAILED DESCRIPTION OF THE PREFERRED EMBODIMENTS

Figure 1A:
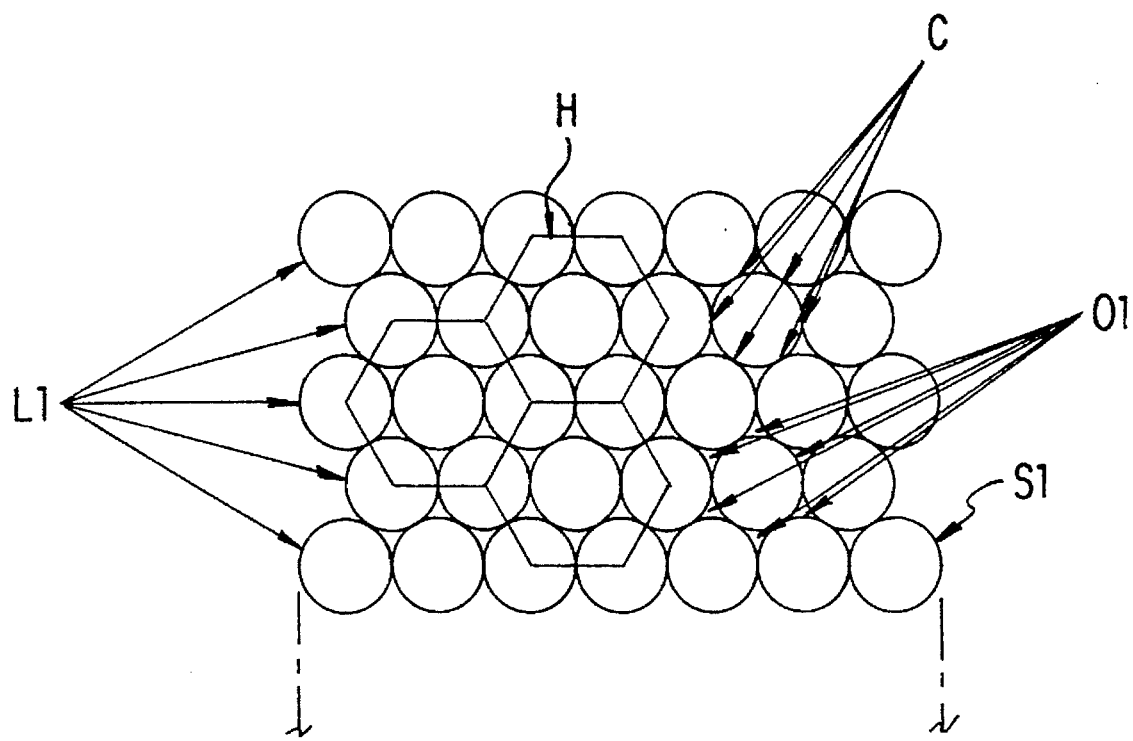
FIGS. 1A and 1B illustrate a top and side view, respectively, of the first layer of the shielding medium according to the invention.

The present invention will now be described with reference to the accompanying Drawings in which like reference characters will identify the same or similar parts throughout the various views.

The present invention is directed to a shielding medium used to protect an object, in particular, the human body, from exposure to electromagnetic fields (EMFs). (It should be noted that as used throughout the instant Specification, the term "electromagnetic field" (EMF) refers to both static and dynamic electric and/or magnetic fields. Moreover, it should be noted that the term "EMF" is intended to cover both non-ionizing and ionizing radiation.) The invention also provides a shielding medium that is air permeable, thereby providing maximum comfort when used in conjunction with a garment worn on the human body. In the alternative, the invention may be used to contain the EMFs emanating from a source itself.

Figure 1B:
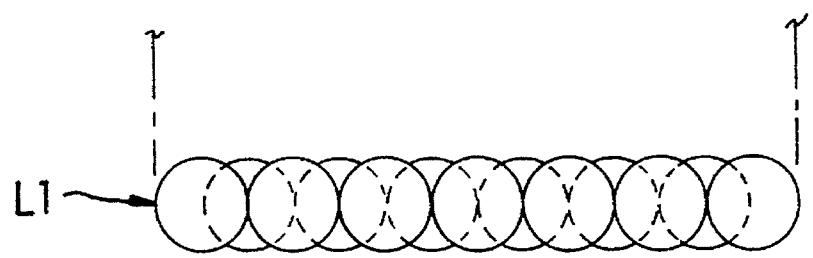

As best shown in FIGS. 1A and 1B, the shielding medium in accordance with the present invention has a first layer L1 composed of a plurality of geometrically shaped objects S1 closely packed together in an array. Preferably, the geometrically shaped objects are in the shape of a hollow sphere S1 (as shown), closely packed in an array that takes the form of one or more hexagons H. Although the spheres S1 in this preferred embodiment are made of copper, it should be apparent that any highly conductive material such as aluminum, gold, silver, magnesium, or even a combination thereof could be used when practicing the present invention. Furthermore, it should be noted that the hollow spheres S1 described herein in this preferred embodiment may easily be replaced with solid spheres or filled with a fluid or other material, if so desired.

Each of the plurality of spheres S1 is in contact with one or more of its neighboring spheres immediately adjacent thereto in the first layer L1. In the preferred embodiment, each of the spheres S1 in the first layer L1, which is not located on the outer periphery of the first layer, is surrounded by and in contact with six other spheres S1 adjacent thereto so as to form the hexagonal arrays H shown in FIG. 1A, thereby leaving six triangular-shaped open spaces O1 around each such surrounded sphere S1. Preferably, the contact C between adjacent spheres is made by a metallic bond achieved by any process known in the art such as spot welding, soldering, molding, etc. The invention as thus constructed provides an excellent shielding medium against exposure to EMFs. Because air can penetrate the medium through openings O1 around the outer dimension of each sphere S1, the medium maintains a degree of air permeability. Thus, a user wearing the shielding medium will experience an increase in comfort over the conventional mediums by using the invention without sacrificing protection against EMFs. Similarly, where the medium is used to contain EMFs emanating from a source, the openings O1 will allow the heat from the source to dissipate without adversely affecting the protection afforded by the shielding medium The closely packed, hexagonal array construction of the first layer L1, however, does not provide a continuous plane due to the plurality of triangular-shaped openings O1 present around portions of the periphery of each sphere S1 in the layer. Although these openings O1 introduce the air permeability characteristic to the first layer L1, the openings O1 also enable some EMFs to penetrate the layer, thereby reducing the maximum effectiveness of the shielding medium.

Figure 2A:
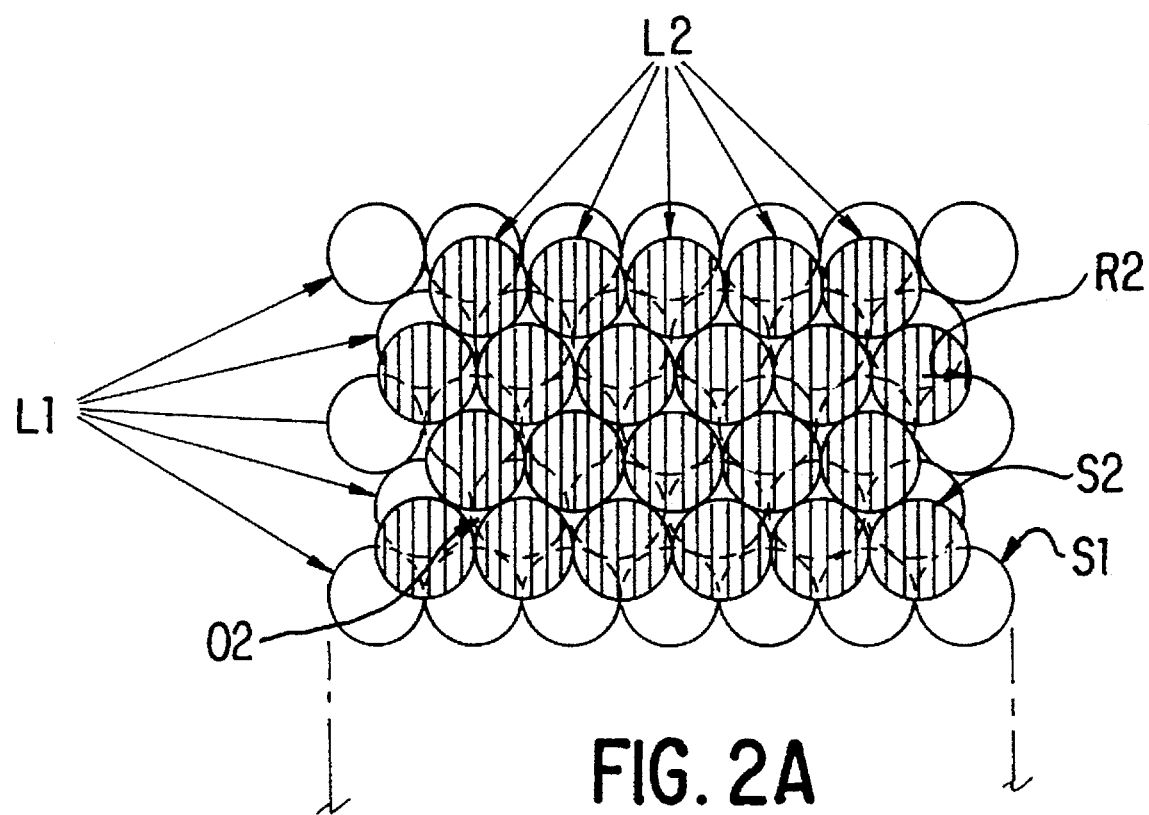
FIGS. 2A and 2B illustrate a top and side view, respectively, of the second layer of the shielding medium according to the invention.
Figure 2B:
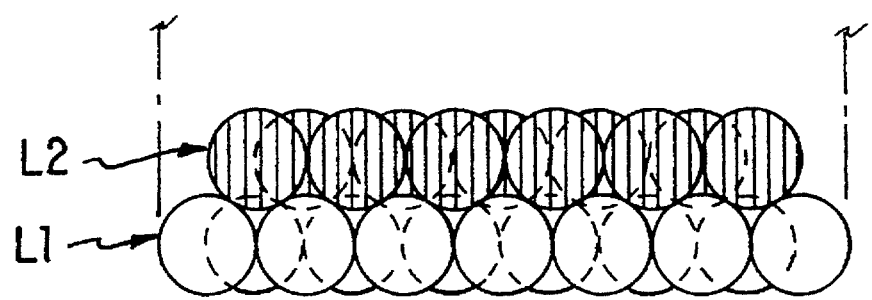

In order to inhibit the penetration of EMFs, a second layer L2 can be superimposed on the first layer L1 of the shielding medium, as shown in FIGS. 2A and 2B. In this preferred embodiment, the second layer L2 is constructed in identical manner as the first layer L1, described above. (For the sake of simplicity, a description of the construction will not be repeated herein.) One distinction should be made, however. That is, the spheres S2 of the second layer must have a radius R2 large enough to ensure that the sphere S2, when superimposed over the opening O1, will not fall through the opening O1. Of course, in the preferred embodiment, the spheres S2 in the second layer L2 have the same radius as the spheres S1 in the first layer L1, as shown in FIGS. 2A and 2B.

In superimposing the layer L2 over the first layer L1, care is taken to position the hexagonal arrays such that each sphere S2 of the second layer L2 is in contact with one or more of the top surfaces of the spheres S1 in the first layer L1. The hexagonal arrays are also positioned such that each sphere S2 is centered directly over one of the triangular-shaped openings O1 in the first layer L1. By superimposing the second layer L2 over the first layer L1 in this manner, approximately half of the triangular-shaped openings O1 in the first layer L1 will be closed. Thus, the shielding effectiveness (SE) of the medium will be increased because the EMFs will only have half as many openings O1 in which to penetrate the shielding medium (SE is given in units of decibels (dB) in accordance with the equation: SE dB=10 log (incident power density/transmitted power density), where the "incident" power density is the power density at a measuring point before the shield is in place and the "transmitted" power density is the power density at the same measuring point after the shield is in place.)

Figure 3A:
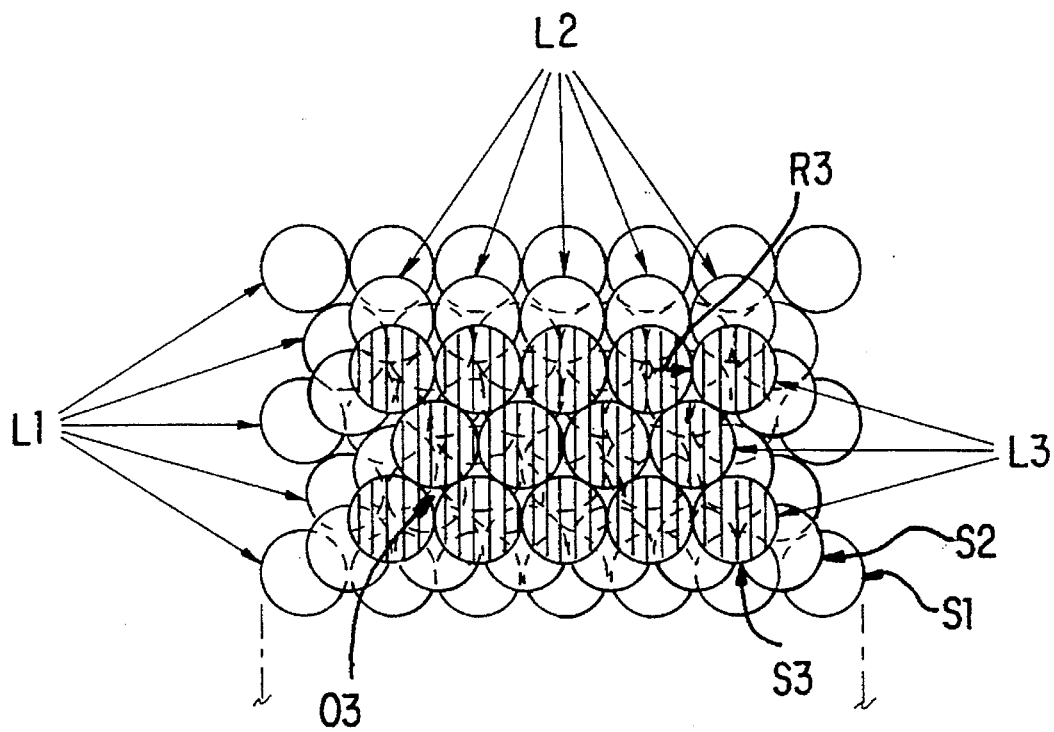
FIGS. 3A and 3B illustrate a top and side view, respectively, of the third layer of the shielding medium according to the invention.
Figure 3B:
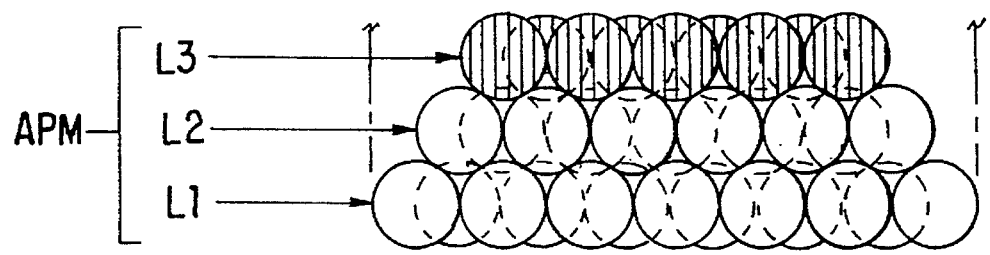

By superimposing yet another layer such as the third layer L3, as shown in FIGS. 3A and 3B, the SE of the shielding medium can be maximized. As with the second layer L2, the third layer L3 is preferably constructed in the same manner as described above for the first layer L1. (Hence, a repetition of this construction will be foregone for the sake of simplicity.) For the third layer L3, however, it is required that the radius R3 of each sphere S3 be large enough to ensure that the sphere, when superimposed over the opening O2 in the second layer L2, will not fall through the opening O2. Of course, in the preferred embodiment, the spheres S3 in the third layer L3 have the same radius as the spheres S2 in the second layer L2, as shown in FIGS. 3A and 3B.

In superimposing the third layer L3 over the second layer L2, the hexagonal arrays should be positioned such that each sphere S3 is centered directly over one of the remaining triangular-shaped openings O1 in the first layer L1. The hexagonal array is also positioned such that each sphere S3 of the third layer L3 is in contact with one or more of the top surfaces of the spheres S2 in the second layer L2. Thus, the shielding effectiveness (SE) of the medium will be maximized because all of the openings O1 in the first layer L1 will be closed.

In order to ensure that the SE of the medium is maximized, it is preferred that the relative positions of the first, second, and third layers L1, L2, L3 remain intact throughout the exposure to EMFs. For example, each of the geometrically shaped objects (e.g., spheres) S2 in the second layer L2, which is located on the outer periphery of the second layer, could be metallically bonded (using one of many well known processes) so as to provide vertical contact with at least one of the geometrically shaped objects S1 on the outer periphery of the first layer L1. Similar vertical contact can be made between these outer peripheral objects S2 and at least one of the geometrically shaped objects S3 on the outer periphery of the third layer L3. Alternative mechanisms may be provided without creating a metallic bond between the three layers, while still ensuring that the three layers remain in their relative positions. For example, a frame (not shown) may be constructed to enclose the outer periphery of the three layers L1, L2, L3, whereby the frame exerts a sufficient force on the three layers to render them immobile.

By constructing the shielding medium as described above, the resulting shielding medium will appear to the surrounding EMFs to be a continuous plane of conductive material, as if the first layer L1 were a solid sheet of material. However, the ambient air will be able to penetrate the shielding medium because of the open space around the outer periphery of each sphere, which allows the air to pass through the first, second and third layers L1, L2, L3. It should be apparent to those skilled in the art that the reflective properties of the material making up the three layers L1, L2, L3, does not allow EMFs to follow the same path as the air. Thus, the shielding medium remains a protective shield impenetrable from the EMFs but completely air permeable. As a result, the shielding medium provides both adequate protection against EMFs (i.e., high SE) and maximum comfort due to its air permeability.

The resulting shielding medium, composed of first, second and third layers L1, L2, L3 is referred to hereinafter as an "Air Permeable Medium (APM)." The particular APM described above using a geometrically shaped object in the form of a hollow (or solid) sphere made of copper (or some other highly conductive material) is primarily effective in reflecting the electric field component of EMFs at frequencies in the range of DC to 100 Giga Hertz (GHz) and also shielding against the magnetic field component of EMFs at frequencies in the range 10 kHz to 100 GHz. (These ranges may vary depending on the conductive material chosen. ) Thus, a conductive air permeable medium, like that described above, will be hereinafter referred to as a "Reflective Air Permeable Medium (RAPM)." RAPMs do not, unfortunately, adequately protect the user from EMFs having low frequency magnetic field components, particularly at frequencies in the range DC to 10 kilo Hertz (kHz).

According to another aspect of the invention, the APM described above can be modified by replacing the highly conductive material (e.g., copper) used above with a magnetically highly permeable material such as the metal alloy known in the art as "Mu-metal." (Two types of "Mu-metal" are commercially available at this time: 1) 79–80% Nickel (Ni), 3.8–5.0% Molybdenum (Mo), and the balance Iron (Fe); and 2) 75–77% Ni, 4–6% Copper (Cu), and the balance Fe.) In the alternative, any other known magnetically highly permeable material such as carbon steel, hipernom (e.g., 80% Ni, 20% Fe), or silicon iron (e.g., 3% Si, 97% Fe) may be used to form the geometrically shaped object (e.g., sphere) used in the first, second and third layers L1, L2, L3.

An Air Permeable Medium (APM) with a geometrically shaped object (e.g., sphere) formed of a magnetically highly permeable material such as Mu-metal will be hereinafter referred to as an "Absorption Air Permeable Medium (AAPM)." Use of the AAPM provides a shielding medium with an excellent absorption shielding against magnetic field components of EMFs in the frequency range of DC to 10 kHz. (This range may vary depending on the magnetically permeable material chosen.)

Figure 4A:
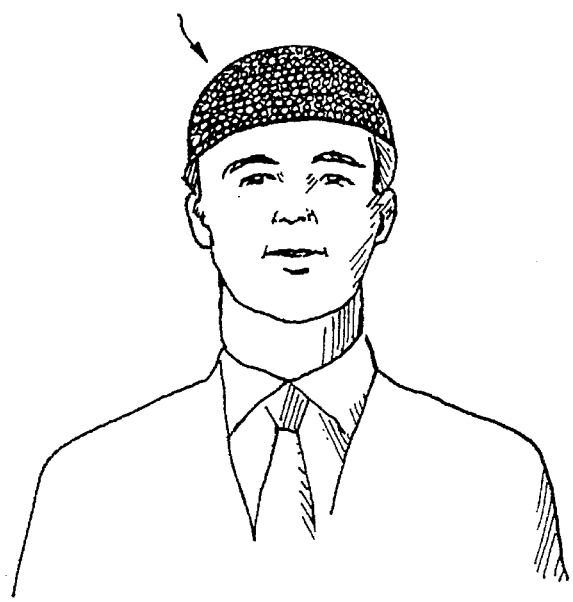
FIGS. 4A and 4B illustrate a front and side view, respectively, of a shielding medium in the form of a helmet using either the RAPM or the AAPM construction according to the invention.
Figure 4B:
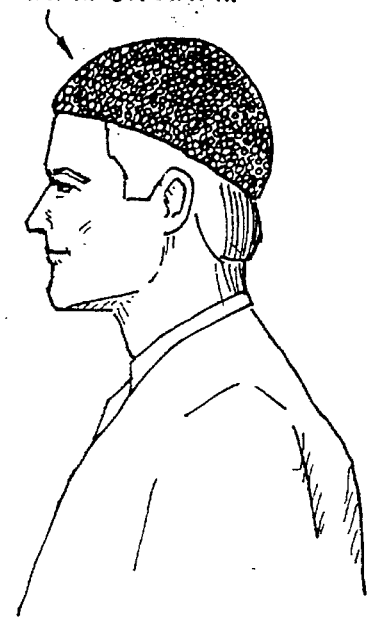
Figure 4C:
FIGS. 4C and 4D illustrate a front and side view, respectively, of a shielding medium in the form of a helmet using a combination of the RAPM and the AAPM construction according to the invention.
Figure 4D:

Using both an RAPM and an AAPM together, as shown, for example, in FIGS. 4C and 4D, provides the most effective shielding medium because of its shielding against both the electric field component of EMFs at frequencies in the range of DC to 100 Giga Hertz (GHz) and also the magnetic field component of EMFs at frequencies in the range DC to 100 GHz. (Another useful definition for Shielding Effectiveness (SE) also expressed in decibels (dB) is the equation: SE dB=R dB+A dB, where "R" is the total reflection shielding and "A" is the total absorption shielding.)

The shielding medium (i.e., RAPM, AAPM, or both), in accordance with another aspect of the invention, can be readily applied to any garment as an insert placed inside an existing garment, as in U.S. Pat. No. 5,115,140, which is hereby incorporated by reference. In the alternative, the garment itself may be made of the shielding medium. For example, FIGS. 4A and 4B illustrate a garment made of either an RAPM or an AAPM worn on a head of a man, whereas FIGS. 4C and 4D illustrate a garment made of an RAPM together with an AAPM worn on the head of a woman. It should be recognized that the head garment made of the shielding medium may take any form, such as a sports cap, a yarmulke, a cowboy hat, or any type of headwear or headpiece.

Generally accepted ratings for shielding effectiveness (SE) can be summarized as follows:

| SE (dB) | Rating |
| --- | --- |
| 120–91 | Highest SE achievable in practical engineering |
| 90–61 | Excellent |
| 60–31 | Good |
| 30–11 | Meaningful |
| 10–0 | Very little shielding |

Figures 8A, 8B:
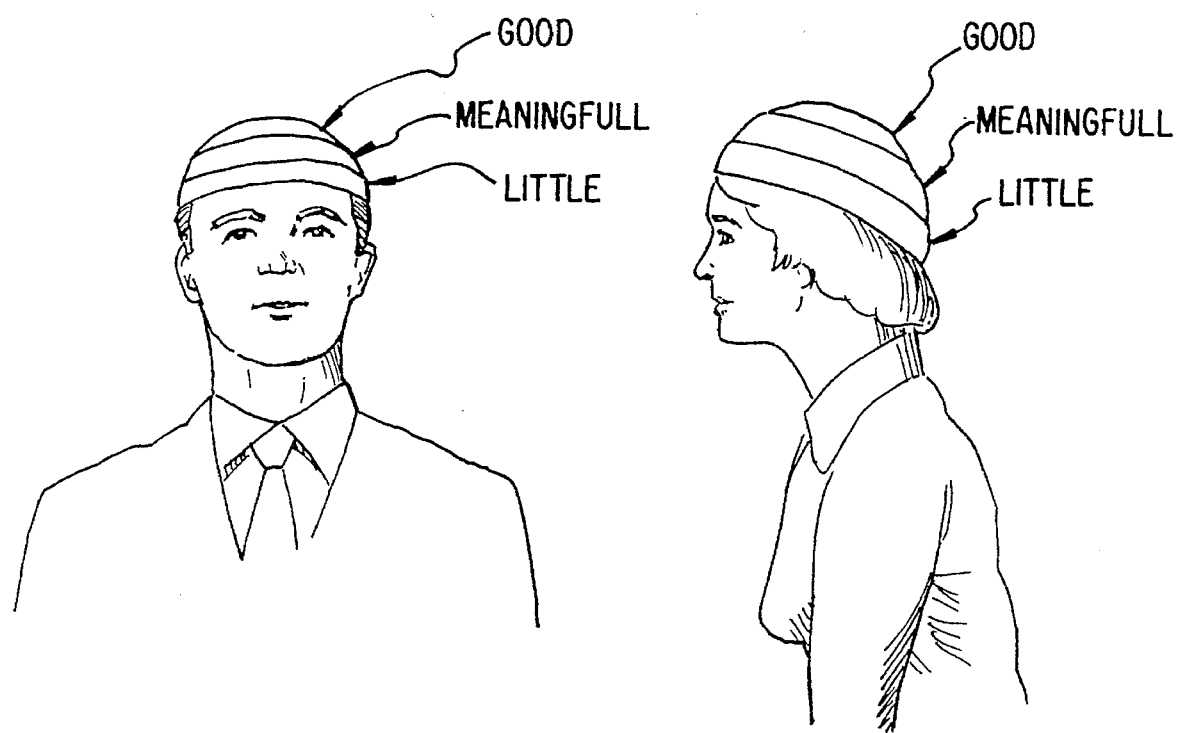
FIGS. 8A and 8B illustrate a front and side view, respectively, of the shielding effectiveness (SE) on the human head as a function of the coverage by the shielding medium.

Depending on the surface area of the APM used to protect the subject's head and the location of the APM on the head, the shielding effectiveness of the RAPM, AAPM, or combination thereof ranges from SE=60 dB to 10 dB. As shown in FIG. 8, this range of SE varies from "good" protection to "little" protection depending on the size and location of the APM used.

Figure 5A:
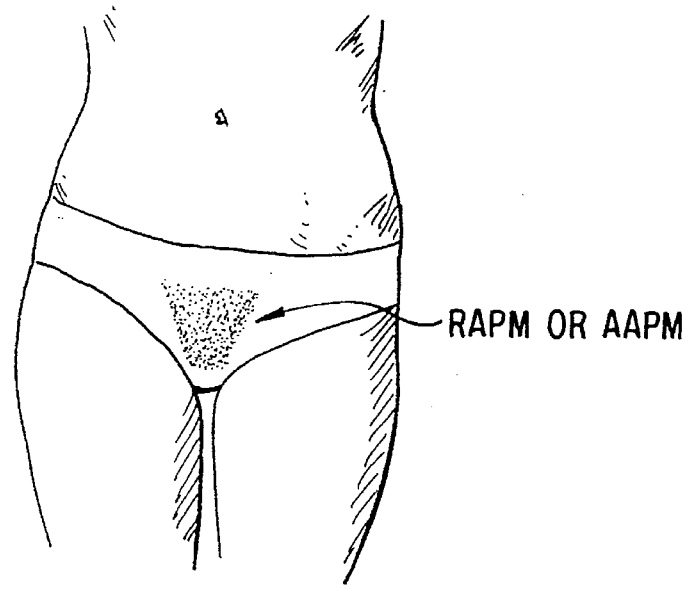
FIG. 5A illustrates a front view of a shielding medium in the form of an undergarment using either the RAPM or the AAPM construction according to the invention.
Figure 5B:
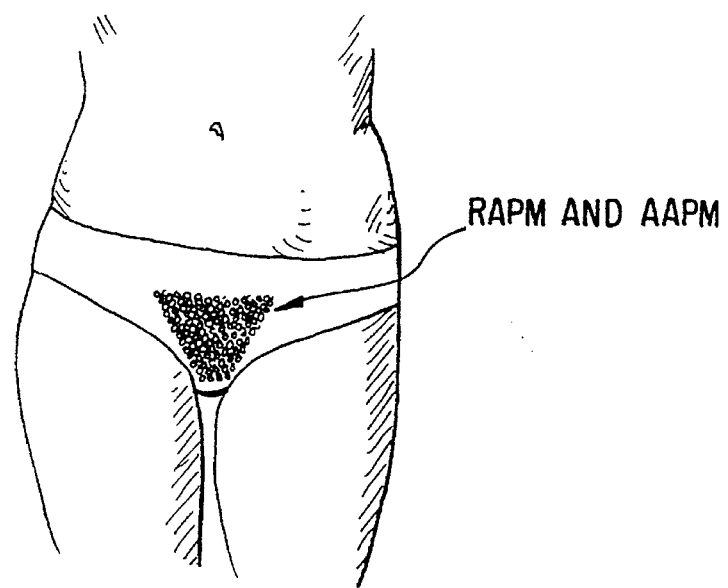
FIG. 5B illustrates a front view of a shielding medium in the form of an undergarment using a combination of the RAPM and the AAPM construction according to the invention.
Figure 6:
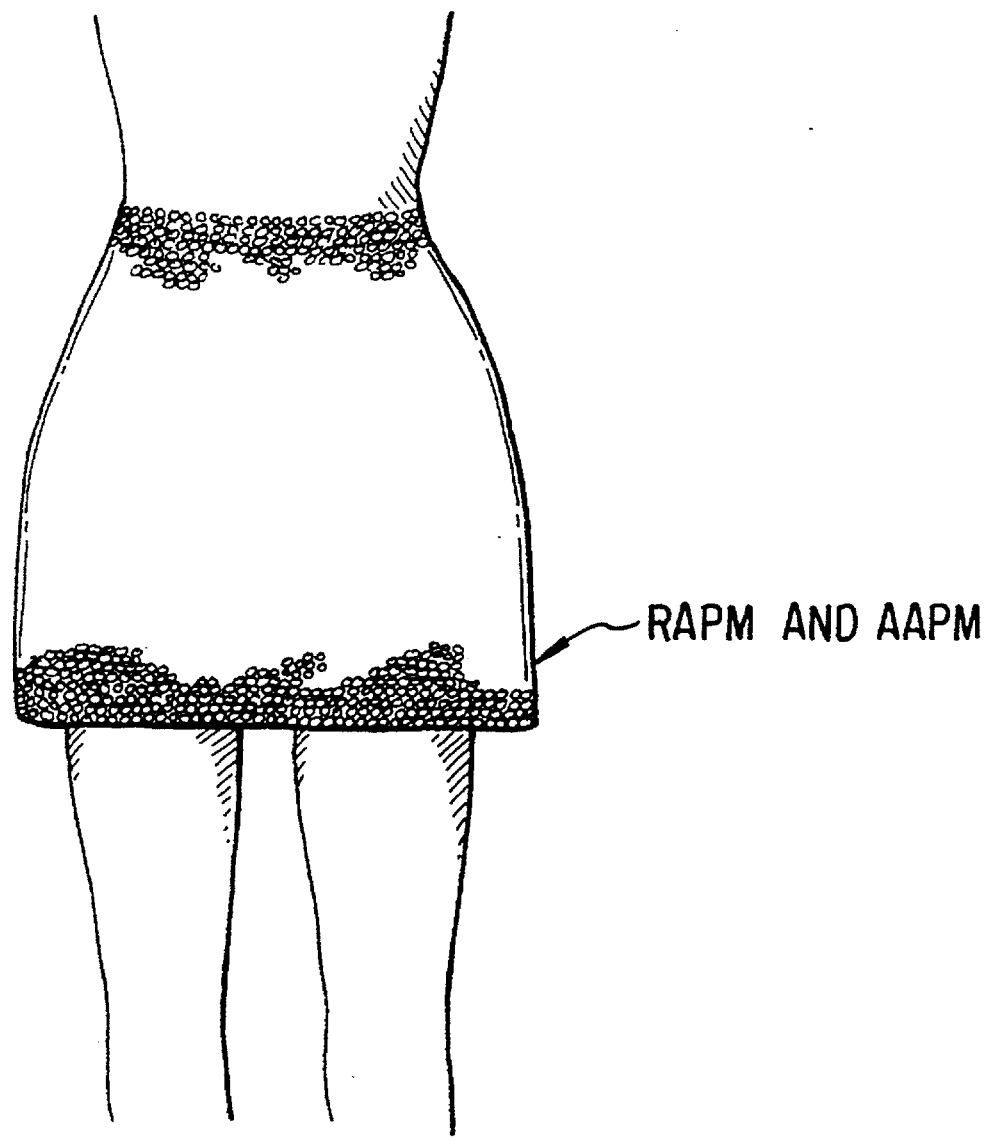
FIG. 6 illustrates a shielding medium in the form of a skirt using a combination of the RAPM and the AAPM construction according to the invention.
Figures 7A, 7B:
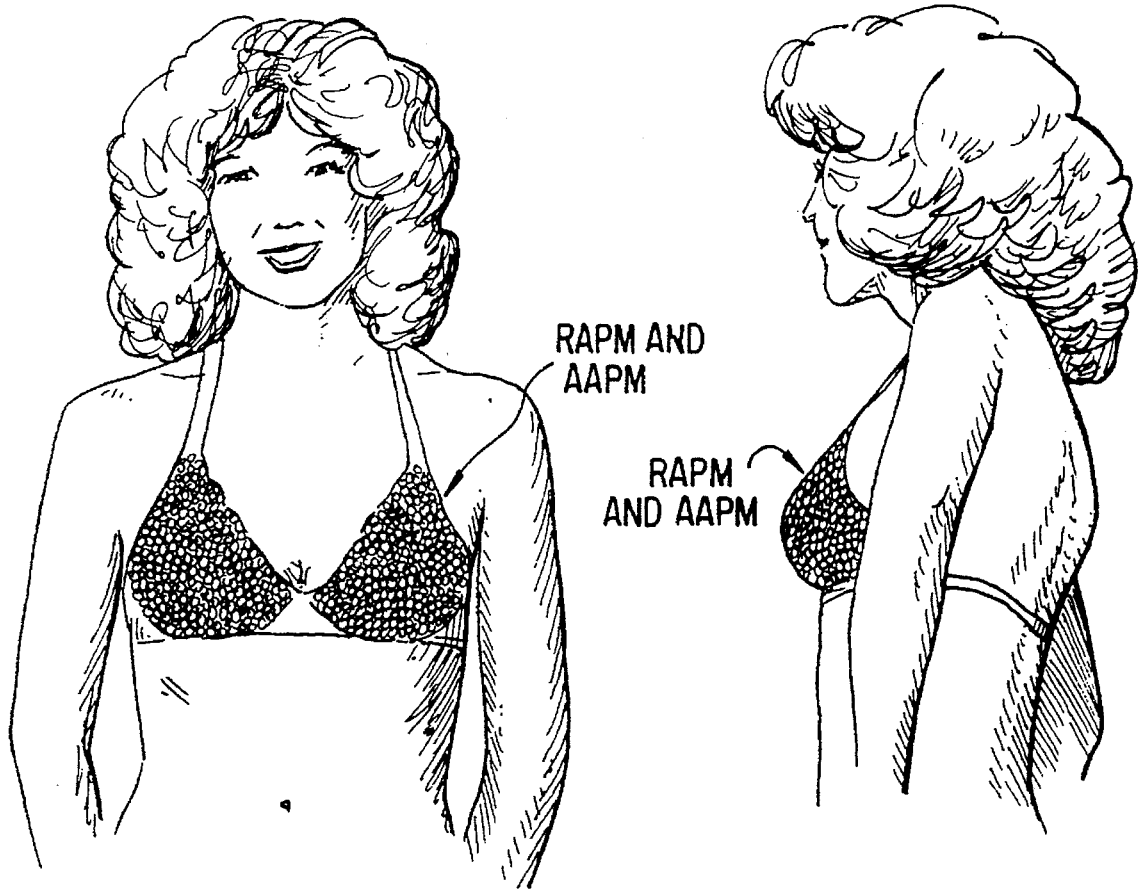
FIGS. 7A and 7B illustrate a front and side view, respectively, of a shielding medium in the form of a brassiere using a combination of the RAPM and the AAPM construction according to the invention.

Additionally, the shielding medium may be used as an insert (or the material itself) for ladies undergarments or brassieres, as shown in FIG. 5A (RAPM or AAPM), FIG. 5B (RAPM and AAPM) and FIG. 7A (RAPM and AAPM), FIG. 7B (RAPM and AAPM), respectively. Furthermore, the shielding medium may be used as an insert (or the material itself) for a skirt, as shown in FIG. 6 (RAPM and AAPM), or any other garment or fashion, such as an apron, maternity clothing, a vest, etc. (Although the preferred embodiments disclosed herein are primarily directed to garments traditionally worn by women, it should be apparent that the shielding medium of the present invention can be incorporated in whole or in part into a garment traditionally worn by, for example, a man, a child, an infant or even an animal.)

Figure 9:
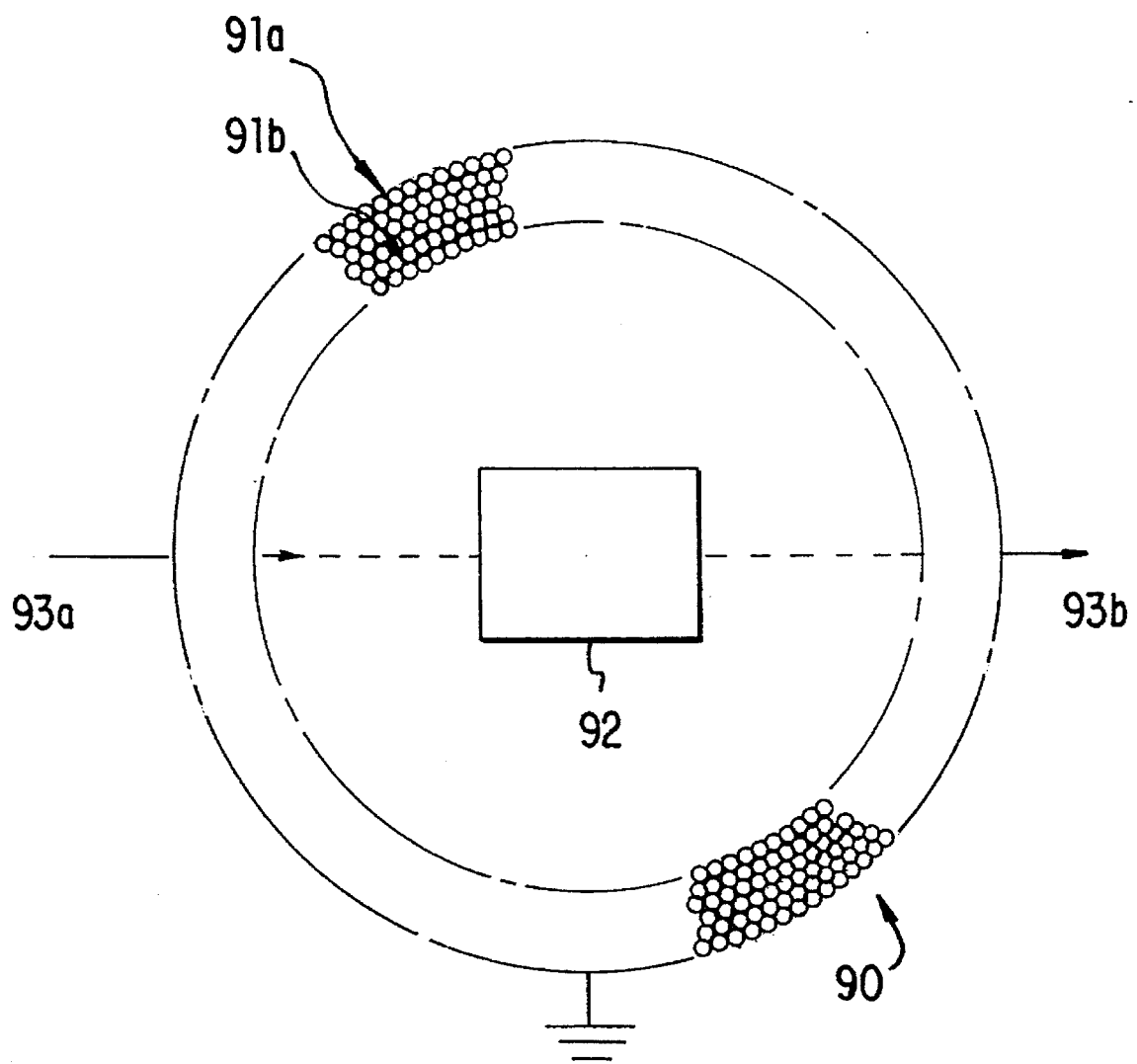
FIG. 9 illustrates a sectional view of the shielding medium containing the EMFs emanating from a source.

In an alternative embodiment, the shielding medium of the invention may be used to contain the EMFs emanating from a source (e.g., that partially or fully surrounds the location of the source 92) itself, as shown in FIG. 9. The shielding medium 90 may take the form of an AAPM 91a, RAPM 91b, or both, as in the previously described embodiments. Because the medium 90 allows air to freely circulate without sacrificing the shielding effectiveness of the material (as discussed above), the source 92 will not lose its ability to dissipate heat. As noted in the Background section above, the source 92 may be any object that emits EMFs (e.g., a cathode ray tube (CRT) in a personal computer). The shielding medium fully accommodates the electrical connections often required for the various sources 93, by allowing the wires 93a, 93b to pass through the openings between the spheres in the shielding medium 90. Although the shielding medium shown in FIG. 9 takes the form of a circle or sphere surrounding the source 92, it should be readily apparent that the shield may take any shape or form (e.g., dome-shaped, box-shaped, etc.).

According to yet another aspect of the invention, the APM described above can be modified by replacing the highly conductive material (e.g., copper) used above with a radiopaque material such as lead or other material used to protect against x-ray, gamma-ray and other ionizing radiation.

As can now be seen from the above description of the preferred embodiments, the invention provides a shielding medium using a multi-layered construction, with each layer containing a plurality of geometrically shaped objects, that appears to the EMFs as a continuous, solid plane, but retains open spaces around the objects for ambient air to circulate. As a result of this construction, the unique shielding medium affords excellent protection against both the electric and magnetic field components of EMFs without sacrificing the comfort of the user (or the heat dissipation of the source).

Although the present invention has been described in detail with reference to the accompanying Drawings, it should be understood that the foregoing Summary, Brief Description, Detailed Description, and Drawings sections are provided for illustrative purposes only. These sections should not be construed as limiting any aspect, object or advantage of the present invention. Instead, various modifications to the preferred embodiments should be readily apparent to those skilled in the art without departing from the spirit and scope of the present invention as defined by the appended claims.

What is claimed is:

1. A shielding medium for protecting an object from exposure to electromagnetic fields, the shielding medium comprising:

a first layer composed of a plurality of geometrically shaped objects;

wherein the plurality of geometrically shaped objects in said first layer are packed in an array such that each geometrically shaped object is in contact with its neighboring geometrically shaped objects adjacent thereto; and wherein said first layer is coupled to the protected object so as to shield the protected object from exposure to the electromagnetic fields;

and further comprising:

a second layer, superimposed over said first layer, composed of a plurality of geometrically shaped objects; and a third layer, superimposed over said second layer, composed of a plurality of geometrically shaped objects;

wherein the plurality of geometrically shaped objects in said first layer have a spherical shape, and wherein said first, second and third layers are together coupled to the protected object so as to shield the protected object from exposure to the electromagnetic fields; and wherein said spherically shaped objects in said second layer are made from Mu-metal.

2. A shield for protecting a portion of the human body from exposure to electromagnetic fields, the shield comprising a conductive component and a magnetically permeable component, wherein:

said conductive component comprises:

a first conductive layer composed of a plurality of geometrically shaped objects made of a conductive material;

a second conductive layer, superimposed over said first conductive layer, composed of a plurality of geometrically shaped objects made of a conductive material; and a third conductive layer, superimposed over said second conductive layer, composed of a plurality of geometrically shaped objects made of a conductive material; and said magnetically permeable component comprises:

a first magnetically permeable layer composed of a plurality of geometrically shaped objects made of a magnetically permeable material;

a second magnetically permeable layer, superimposed over said first magnetically permeable layer, composed of a plurality of geometrically shaped objects made of a magnetically permeable material; and a third magnetically permeable layer, superimposed over said second magnetically permeable layer, composed of a plurality of geometrically shaped objects made of a magnetically permeable material;

wherein said conductive component and said magnetically permeable component are together coupled to the human body so as to shield a portion of the human body from exposure to the electromagnetic fields.

3. The shield of claim 2, wherein said conductive component is overlaid on said magnetically permeable component such that the magnetically permeable component is closest to the protected portion of the human body.

4. The shield of claim 2, wherein all of the geometrically shaped objects in said first, second and third conductive layers are spherical in shape and made of aluminum.

5. The shield of claim 2, wherein all of the geometrically shaped objects in said first, second and third magnetically permeable layers are spherical in shape and made of carbon steel.

* * * * *